US007735355B2

(12) United States Patent
Lüchinger

(10) Patent No.: US 7,735,355 B2
(45) Date of Patent: Jun. 15, 2010

(54) GRAVIMETRIC MOISTURE MEASUREMENT INSTRUMENT

(75) Inventor: Paul Lüchinger, Uster (CH)

(73) Assignee: Mettler-Toledo AG, Greifensee (CH)

( * ) Notice: Subject to any disclaimer, the term of this patent is extended or adjusted under 35 U.S.C. 154(b) by 243 days.

(21) Appl. No.: 11/769,460

(22) Filed: Jun. 27, 2007

(65) Prior Publication Data
US 2008/0006082 A1    Jan. 10, 2008

(30) Foreign Application Priority Data
Jul. 7, 2006    (EP) .................................. 06116841

(51) Int. Cl.
*G01N 5/02* (2006.01)
(52) U.S. Cl. .......................................................... 73/73
(58) Field of Classification Search ...................... 73/73
See application file for complete search history.

(56) References Cited

U.S. PATENT DOCUMENTS 2,042,855 A * 6/1936 Merklein ..................... 219/542
2,305,014 A * 12/1942 Langel Adrien L ........ 220/23.6
5,425,126 A * 6/1995 Lee ............................. 416/95
5,485,684 A    1/1996 Philipp et al.
6,920,781 B2    7/2005 Olesen

FOREIGN PATENT DOCUMENTS

DE    3305846 A1    8/1984
JP    04194554    *    2/1992    ............... 219/677

* cited by examiner

*Primary Examiner*—Hezron Williams
*Assistant Examiner*—Alex Devito
(74) *Attorney, Agent, or Firm*—Stanley Law Group LLP

(57) ABSTRACT

A measuring instrument for gravimetric moisture determination of a sample has a radiator, a weighing cell, and a sample receiver which can be connected to the weighing cell. The sample receiver allows the sample to be placed on or removed from the sample receiver. The radiator is positioned either above or below the sample, or both above and below, relative to the load direction of the weighing cell. A rotatably mounted heat conductor whose axis of rotation is orthogonal to the plane in which the sample or the sample receiver extends is positioned between the radiator and the sample. The heat conductor absorbs at least part of the radiation that impinges upon it and releases the absorbed radiation to the sample through at least one radiation-releasing surface. Through its ability to rotate, the heat conductor irradiates the entire sample surface.

19 Claims, 4 Drawing Sheets

GRAVIMETRIC MOISTURE MEASUREMENT INSTRUMENT

CROSS-REFERENCE TO RELATED APPLICATIONS

This application claims a right of priority under 35 USC §119 from European patent application 06116841, filed 7 Jul. 2006, the content of which is incorporated by reference as if fully recited herein.

TECHNICAL FIELD

The present invention relates to a measuring instrument for the gravimetric determination of moisture content.

BACKGROUND OF THE ART

To determine the moisture content in a sample, the sample is dried and the weight of the sample is measured before and after the drying process. Due to the extensive amount of work involved, this method is very expensive as well as error-prone.

In some cases, the weight loss can also be measured during the drying process. In a given sample, the decrease in weight is a function of the temperature, the length of the drying time, and the conditions in the test compartment, and it conforms to a curve representing the sample weight as a function of the elapsed drying time which asymptotically approaches the dry weight of the sample. The curve for the given sample is determined by comparative experiments and can be expressed mathematically through an approximation formula. A measuring instrument for gravimetric moisture determination which is appropriately equipped with available electronic technology can compute the moisture content of a sample based on the measured parameters of the aforementioned curve and based on the length of the drying time and indicate the result on a display unit. With this method, the substance to be dried does no longer need to be totally desiccated; it is sufficient to determine the coordinates of two measurement points in the weight-versus-time diagram.

As has already been mentioned at the beginning, the weight change of a sample is substantially a function of the temperature, the length of the drying time, and the conditions in the test compartment. Especially the stringent requirements imposed on the test compartment and its design features are setting a limit to the accuracy of the commercially available instruments.

The term "test compartment" in the present context means a space which is enclosed by the housing of the measuring instrument and which can be opened in order to insert or remove a sample. Also arranged inside the test compartment are a sample receiver and a means to heat the sample. The sample receiver is connected to a gravimetric measuring instrument.

Normally, the sample is spread in a thin layer onto a flat sample receiver, for example a sample tray. The tray is preferably arranged in the measuring instrument for gravimetric moisture determination in such a way that the sample-carrying area is horizontally leveled, so that samples of low viscosity cannot collect at the lowest point (relative to the direction of the load) of the sample tray.

As a means for heating the sample, a variety of radiation sources are used, such as heat radiators, microwave generators, halogen- and quartz lamps. A gravimetric moisture-determination instrument of the aforementioned type is disclosed in commonly-owned U.S. Pat. No. 5,485,684, issued 23 Jan. 1996 to Philipp, et al. In this instrument, the sample substance is put on the weighing pan while the latter is outside of the gravimetric moisture-determination instrument. To do this, the balance is pulled out of the housing of the measuring instrument on a sliding carrier like a drawer. For a radiation source, a ring-shaped halogen lamp is used which is located above the sample receiver when the instrument is in its operating condition.

As was found in experiments, the type and the design configuration of the radiation source being used are among the primary causes for inaccurate measurement results in existing gravimetric moisture-determination instruments. For example, radiators with perforations or radiators whose radiation originates substantially from a point or a line can cause a non-uniform irradiation of the sample with the result that the energy density in individual spots of the sample can be so high as to cause in some places a thermal breakdown of the sample.

If the radiator spans over the sample in a spread-out and largely flat configuration, it is possible that a moisture-saturated gas cushion will form between the sample and the radiator and remain in place, whereby a further escape of moisture from he sample is prevented. Such an obstruction to the drying process could have a significant effect on the drying time, wherein in particular the temperature-related random atmospheric convection between the radiator and the sample enter into the measuring result.

The errors in the drying time that are caused by the obstruction in the drying process, and/or the measurement errors in the sample weight values due to thermal decomposition impose a limit on the accuracy that can be obtained in an analysis with the aforementioned mathematical model. As an alternative to using the mathematical model, one can use the known method in which all of the moisture—to the extent that this is possible—has to be driven out of the sample. However, this requires a very long drying time, which increases the risk that a thermal decomposition or oxidation of the sample will occur as a result of the long, sustained exposure to the heat radiation of the radiators.

For the reasons that have just been explained, it is hardly possible to determine an absolute value for the moisture content with a gravimetric moisture-determination instrument. For a more accurate determination of the moisture content of a substance or for the calibration of dryers, the known Karl Fischer titration method is therefore still in use. This method is very labor-intensive, prone to user errors, and expensive.

It is therefore the object of the present invention to provide a gravimetric moisture-determination instrument with a radiator that has an improved distribution of the radiation over the sample. Furthermore, the escape of moisture from the sample should not be compromised as a result of the improved distribution of the radiation.

SUMMARY OF THE INVENTION

According to the invention, this objective is met with a measuring instrument for the gravimetric determination of moisture in accordance with claim 1.

The measuring instrument for gravimetric moisture determination according to the invention includes at least one radiator, a weighing cell, and a sample receiver which can be connected to the weighing cell. The sample receiver is of a configuration that allows a sample to be placed on or removed from the sample receiver. The at least one radiator is arranged, relative to the direction of the load, above and/or below the sample. This means that a radiator can be arranged above the sample, below the sample, and also above as well as below the sample. A rotatably supported heat conductor is arranged between each radiator and the sample, wherein the rotary axis of the heat conductor is oriented orthogonal to the surface area over which the sample or the sample receiver extends. The radiation of the radiator can at least in part be absorbed by the heat conductor; the absorbed radiation can be delivered to the sample as heat radiation through a radiation-releasing surface of the heat conductor; and at least as a result of the rotation of the heat conductor the entire surface of the sample can be irradiated. Thus, the function of the heat conductor in the measuring instrument according to the invention is not limited to absorbing and releasing heat radiation. According to the invention, the heat conductor can also serve to absorb other kinds of radiation such as for example electromagnetic radiation and to convert it into heat radiation which is delivered to the sample by way of the radiation-releasing surface. It is also not necessary for the heat conductor to span over the entire area occupied by the sample, as the rotating heat conductor sweeps over the entire surface of the sample without touching the latter, whereby the heat radiation is distributed over the sample in an approximately uniform manner.

The term "heat conductor" means a device with at least one place through which it can absorb radiation energy, and with a radiation-releasing surface through which the radiation energy is released again in the form of heat radiation with an approximately uniform distribution. To perform this function, it is irrelevant whether the radiator is arranged in fixed connection with the housing and separate from the heat conductor, or whether the radiator is integrally incorporated in the heat conductor.

To achieve a uniform distribution of the heat radiation, the radiation-releasing surface through its entire rotary sweep preferably keeps the same distance from the plane in which the sample is spread out. It is therefore advantageous if the heat conductor is designed with a flat surface in a plane that is orthogonal to the axis of rotation, wherein the radiation-releasing surface coincides in essence with the flat surface of the heat conductor that faces towards the sample. It is further advantageous if the rotary axis of the heat conductor is arranged parallel to the direction of the load.

The radiation-releasing surface of the heat conductor is preferably a circular surface whose area substantially equals the flat area over which the sample is spread out. As a result, the radiator is to a large extent protected by the heat conductor against contamination by the rising gases, if the heat conductor has no perforations or is not made of a gas-permeable material.

If the radiator is arranged directly in the heat conductor, the at least one heat conductor can also be sector-shaped.

In a first embodiment, the heat conductor can have perforations and/or incisions oriented preferably in the direction of the load, to prevent that the moisture escaping from the sample during a drying process becomes trapped in a gas cushion between the heat conductor and the sample and thereby has a negative effect on the drying process.

In a second embodiment, the heat conductor can also consist of a porous material allowing the passage of gas in the direction of the load. This likewise achieves the purpose that the moisture which has left the sample cannot remain above the surface of the sample.

The heat conductor in a third embodiment can have at least one perforation or a incision designed in such a way that at least one transverse member in the shape of a propeller blade or a scoop is formed on the heat conductor. With this at least one transverse member a moving stream can be produced in the gaseous medium preferably against the direction of the load, whereby the moisture-enriched gaseous medium is removed from the vicinity of the sample.

As the radiation-releasing surface of the radiator is set into rotation, parts of the gas cushion in the immediate vicinity of the radiation-releasing surface are dragged along and, as a result of the centrifugal force, are pushed out into the border area of the radiation-releasing surface. From there, the moisture-enriched medium that has been moved into the border area can be picked up and removed for example by the flow current of a suction device. As another possibility, the heated gaseous medium is displaced from the immediate vicinity of the sample receiver in the border area by an inflow of cold, and therefore heavy, gaseous medium. As a result, the warm, gaseous medium rises up in the test compartment and leaves the latter through ventilation slits, as known from the existing state of the art. As a means to improve the removal rate with the same speed of rotation of the heat conductor, the radiation-releasing surface of the heat conductor can be equipped with at least one ridge, groove, channel or depression.

In order to deliver the heat radiation with uniform intensity over the entire radiation-releasing surface, at least part of the heat conductor should include materials of good thermal conductivity such as for example aluminum, alloys of aluminum, ceramics, or glass. If the radiation source generates an alternating electromagnetic field, the heat conductor can consist entirely or partially of a ferromagnetic material such as for example an iron plate. The alternating electromagnetic field induces eddy currents in this iron plate, which will cause the latter to heat up. Depending on the design of the heat conductor, the surface of the latter can be provided with surface coatings. To improve corrosion resistance and radiation-emitting properties, a heat conductor of aluminum could for example be covered with a black-colored oxide layer.

Ideally, the heat conductor is connected to a drive source through a shaft that runs in one or more bearings which are rigidly connected to the housing. The drive source can be a motor, but it is also conceivable to use passive drive sources which make use of the gas flow patterns that exist in the housing. It is also possible to drive the rotation of the heat conductor by way of a gear stage. In this case, the heat conductor can be supported in the housing by way of ring of roller balls (comparable to a turntable), which is also referred to herein as a ball bearing ring. This has the advantage that in the center of the heat conductor there is no shaft whose radiation intensity would be different from the rest of the heat conductor. Of course, instead of the ring of roller balls it is also possible to use an appropriate kind of sliding ring bearing.

Depending on the material properties of the sample, it is possible even with gentle heating that parts of the sample will sublimate or decompose. Such decomposition products have a tendency to settle on the hot parts of the radiator or of the heat conductor, where they will form an insulating layer. Therefore, the heat conductor is preferably connected through releasable fastener elements to the shaft or to the ball bearing ring. This allows the heat conductor and, if applicable, the radiator to be uninstalled for cleaning and subsequently reinstalled without a problem. Releasable fastener elements that can be used for this purpose include for example bolts, pins, screws, and also snap-locking elements such as bolts with locking balls, spring clips, ball detents and the like. If the heat conductor is supported by means of a ball bearing ring, it can be uninstalled for cleaning and subsequently reinstalled by simply lifting it out and setting it back in place.

As a radiator one can use for example a heating plate, a heating foil, a heat radiator, an induction coil, a halogen lamp, or a quartz lamp.

Depending on the radiator that is being used, the radiation originates essentially from a point or from a line and distributes itself through the entire test compartment. As a result, parts of the measuring instrument are also heated, rather than only the sample, which can cause energy losses and also have an influence on the measuring device, in particular the weighing cell. It can therefore be of practical benefit if the radiator is in addition arranged inside a radiation-guiding body which guides the radiation, so that the heat conductor can absorb heat for example over a larger surface. This condition is met for example by heating plates and by heating foils that are installed on flat metal bodies. Due to their metallic properties, local variations in heat generation are balanced out already within the metal body, so that the heat radiation can be transmitted to the heat conductor with a more uniform intensity and through a larger surface area. If for example an infrared- or halogen lamp is used as a radiation source, the radiation-guiding body can also be a hollow body that is open at least on one side and whose internal surface is for example provided with a reflective surface. Depending on their design, radiation-guiding bodies of this kind can focus, disperse, channel or otherwise shape the radiation, depending on how the radiation source and the heat conductor are configured. In most cases the basic shapes of the radiation-guiding bodies are rotationally symmetric.

BRIEF DESCRIPTION OF THE DRAWINGS

Details of the measuring device according to the invention can be found in the following description of the embodiments illustrated in the drawings, wherein identical parts are identified with identical reference numerals and wherein:

FIG. 3b is a top plan view of the radiation-releasing surface of FIG. 3a as seen in the direction Z that is indicated in FIG. 3a;

DETAILED DESCRIPTION OF A PREFERRED EMBODIMENT

Figure 1:
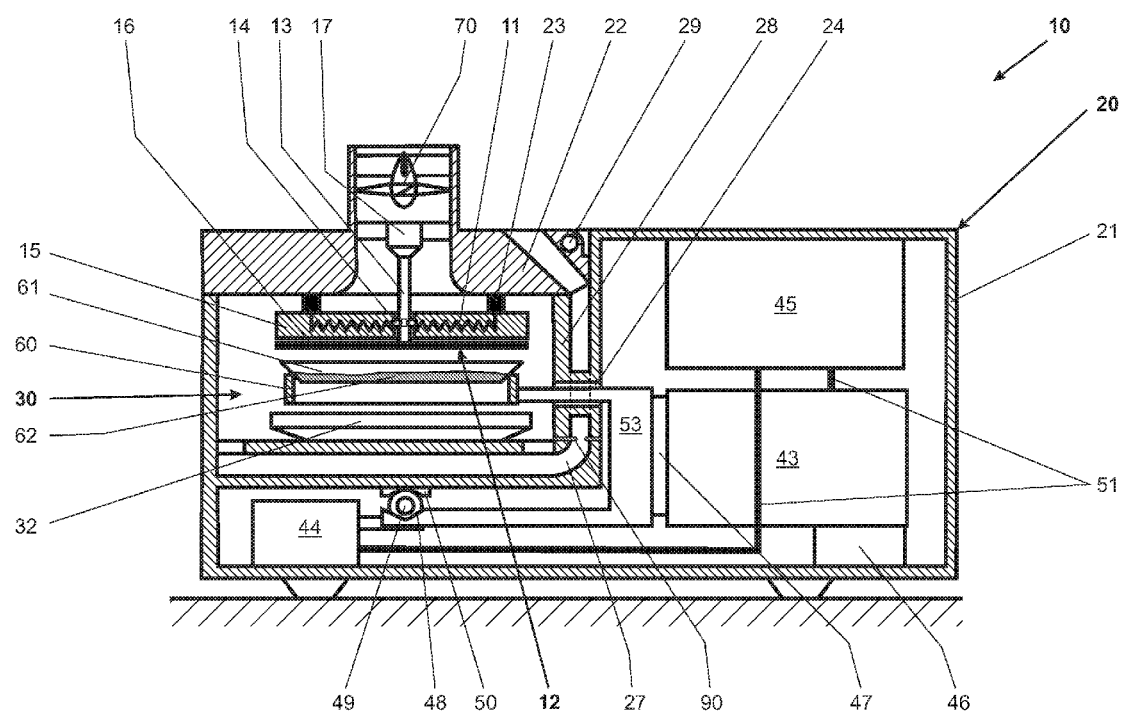
FIG. 1 is a side sectional view of a measuring device with a housing in which the test compartment and the weighing cell are arranged side-by-side, and with the radiator installed in a lid which is hinged on the housing so that it can be raised or lowered on a substantially horizontal hinge axis, as well as with a suction device incorporated in the lid and with an insulating ventilation duct arranged between the weighing cell and the test compartment.

FIG. 1 shows a sectional view of a measuring instrument 10. The measuring instrument 10 has a housing 20 in which a test compartment 30 is arranged. The housing 20 is divided into a movable housing part 22 and a stationary housing part 21. Arranged in the stationary housing part 21 are a weighing cell 43, a calibration-weight-handling mechanism 44, and at least one electronic module 45, all of which are connected to each other by communicating means 51. The electronic module 45 contains at least one signal-processing module that is not shown in detail, and possibly also a control- and/or regulation module. The weighing cell 43 has at least a stationary portion 46 and a load-receiving portion 47. Known types of weighing cells are for example elastically deforming bodies carrying strain gauges, or weighing cells based on the principle of electromagnetic force compensation, or weighing cells with oscillating strings, capacitative weighing sensors and the like. The stationary portion 46 is rigidly connected to the stationary housing part 21. Arranged on the load-receiving portion 47 is a connecting member 53 which connects a sample receiver 60 to the load-receiving portion 47. As illustrated, a sample tray 61 with a sample 62 can be set on the sample receiver 60. With a suitable design of the sample receiver 60, one could of course also put the sample 62 directly on the sample receiver 60.

Further, a calibration weight receiver seat 48 is formed on the connecting member 53. A calibration weight 49 can be put on the weight receiver seat 48 by means of the calibration-weight-handling mechanism 44 actuated either by the user or under the control of the measuring instrument 10, in order to determine a correction value for the measuring signal based on the current operating condition of the measuring instrument 10. After the correction value has been determined, the calibration weight 49 is disconnected again from the calibration weight receiver seat 48 and held by the calibration-weight-handling mechanism 44 against a resting cradle 50 until the next calibration cycle takes place. Ideally, as a way to avoid eccentric load errors in the correction value, the mass center of the calibration weight 49 or—if applicable—the combined mass center of a plurality of calibration weights 49 lies close to an axis that passes through the center of gravity of the sample receiver 60 and/or of the sample tray 61 and/or the sample 62. The term "eccentric load error" (also referred to as corner load error) means the deviation that occurs in the weight measured by a weighing device for one and the same load when the latter is placed eccentrically on the sample receiver 60 in comparison to when it is put in a centered position.

As illustrated in FIG. 1, the movable housing part 22 is configured as a lid in which a radiation source 11 is arranged. A hinge 29 in the upper part of the housing 20 connects the movable housing part 22 to the stationary housing part 21, with the axle of the hinge 29 being arranged substantially horizontal. The movable housing part 22 forms the upper part of the test compartment 30. FIG. 1 shows the measuring instrument 10 in operating position, meaning that the lid of the test compartment 30 is shown in the closed position.

The radiator 11 in the illustrated embodiment is enclosed by a radiation-guiding body 15 which has a bearing 14 formed at its center. The radiation-guiding body 15 is connected through support posts 23 to the movable housing part 22. Inside the radiation-guiding body 15 there can be heat radiators, heating foils, microwave generators, halogen- and quartz lamps arranged as radiation generators. In the illustrated embodiment a disk-shaped heat conductor 16 with the radiation releasing surface 12 is arranged between the radiator 11 and the sample 60. The heat conductor is connected to a shaft 13 which is rotatably supported in the bearing 14. The disk 16 consists preferably of a material with good thermal conductivity. Due to its thermal conductivity and density as well as the advantages of being easy to work with and resistant to corrosion, it is very advantageous to use aluminum and aluminum alloys. The aluminum parts are preferably given a coating, ideally a black-colored oxide layer. However, the heat conductor 16 can also be made of ceramic materials or glass. The axis of rotation of the shaft 13 is oriented in the direction of the load. The end of the shaft 13 that faces in the direction of the load is connected to the heat conductor 16 with the radiation-releasing surface 12 whose shape and size essentially match the shape and size of the area filled by the sample 62. In the radiation-guiding body 15 radiation is generated, essentially heat radiation which is transmitted to the heat conductor 16 which, in turn, releases the radiation to the sample 62 through the radiation-releasing surface that faces towards the sample. During the drying process, the heat conductor 16 is set in rotation by a drive mechanism 17 whose description follows. Due to the flat and planar configuration of the radiation-releasing surface 12, its parallel alignment with the sample 62, its rotary movement, and the structure of its surface which is matched to the distance from the sample 62, the radiation emitted in the direction of the load by the radiation-releasing surface 12 can heat the sample 62 in a uniform manner.

Figure 3A:
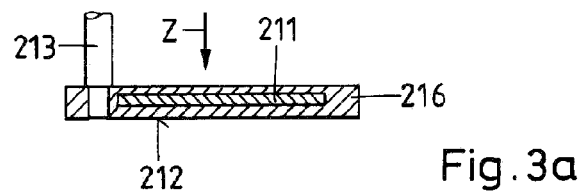
FIG. 3a is a side sectional view of a heat conductor in which a radiator is incorporated.
Figure 3B:
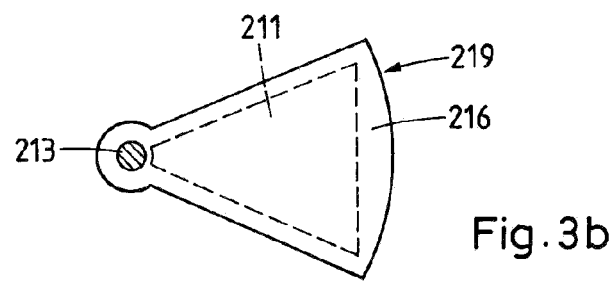

Of course, designs are also possible in which the entire radiator 11 is arranged directly in or on the heat conductor 16, as is shown in FIGS. 3a and 3b. However, providing the radiator 11 with power becomes more involved with this design version. The supply with electrical power can be accomplished for example by way of a collector with carbon brushes or contact-free by means of electromagnetic induction.

A suction device 70 is incorporated above the radiator 11 in the movable housing part 22. The suction device 70 consists of a static assembly in which a motor is incorporated, and of an axial rotor. In this embodiment, the shaft 13 of the preceding description is connected to the motor 17. Of course, the shaft 13 can also be connected directly or through a gearbox to the drive source of the suction device 70, in which case the separate motor 17 would be omitted. If a stream of the gaseous medium of sufficient volume and velocity flows through the test compartment 30 against the direction of the load, the heat conductor 16 can also be equipped with blades or scoops similar to a turbine wheel of an axial turbine. In this case, the gas stream moving through the blades will set the heat conductor 16 in rotation.

The lower part of the test compartment 30 is formed in the stationary housing part 21. The connecting member 53 which is mechanically connected to the weighing cell 43 protrudes likewise into the lower part of the test compartment 30, so that the sample receiver 60 which is connected to the connecting member 53 is arranged entirely in the test compartment 30. To provide thermal insulation, a wall 28 of the stationary housing part 21 between the weighing cell 43 and the test compartment 30 is configured at least in part as a double wall. With the double-walled configuration of the wall 28, a ventilation duct 27 is formed through which a gaseous medium can be directed into the test compartment 30. The medium flowing through the duct during the measuring process cools the wall 28, so that the heat radiated from the test compartment 30 cannot penetrate into the part of the housing that contains the weighing cell 43. Of course, the gaseous medium conducted through the ventilation duct 27 does not necessarily have to be introduced into the test compartment 30. In this regard, it is also possible to use a simple ventilation duct of the kind disclosed in U.S. Pat. No. 6,920,781 B2.

There can further be a second radiator 32 arranged in the test compartment 30 below the sample receiver 60. Since the radiation from the second radiator 32 is directed at the bottom of the sample tray 61 and since the latter consist in most cases of a heat-conductive material which in itself has a certain distributing effect, there is no absolute necessity for arranging a second rotatably supported heat conductor between the second radiator 32 and the sample 62. Of course, this feature can still be adopted in the design, if it appears advisable in the interest of achieving an even better radiation distribution.

There can further be various auxiliary devices arranged in the ventilation duct 27. For example, the gaseous medium can be ionized by means of an ionizer 90 in order to eliminate electrostatic charges inside the test compartment 30. To allow the connecting member 53 to protrude into the test compartment, the wall 28 has a passage opening 24. This passage is configured as a closed tubular conduit, so that the medium streaming through the ventilation duct 27 cannot enter into the test compartment 30 through the passage 24 nor exert a force on the connecting member 53.

Figure 2A:
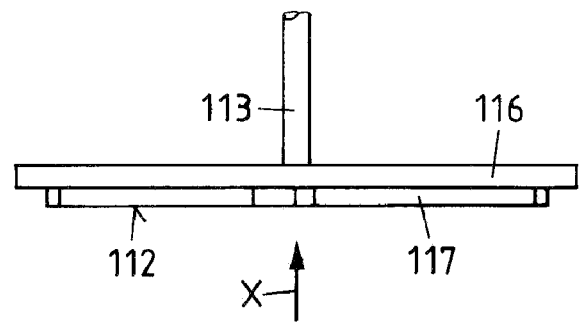
FIG. 2a is a side sectional view of the radiation-releasing surface, shown as an enlarged detail of FIG. 1, and equipped with ridges.

The heat conductor 116 that is shown in a sectional view in FIG. 2a is identical to the disk in FIG. 1, except for the ridges 117 that have been added to the radiation-releasing surface 112. In principle, there are no constraints imposed on the shape of these ridges. However, to meet the simultaneous requirements for the best possible removal of the moisture-enriched gaseous medium and the best possible uniformity of the radiation intensity, certain configurations are preferred, two of which are represented in FIGS. 2b and 2c in plan view as seen in the direction X indicated by the arrow in FIG. 2a.

Figure 2B:
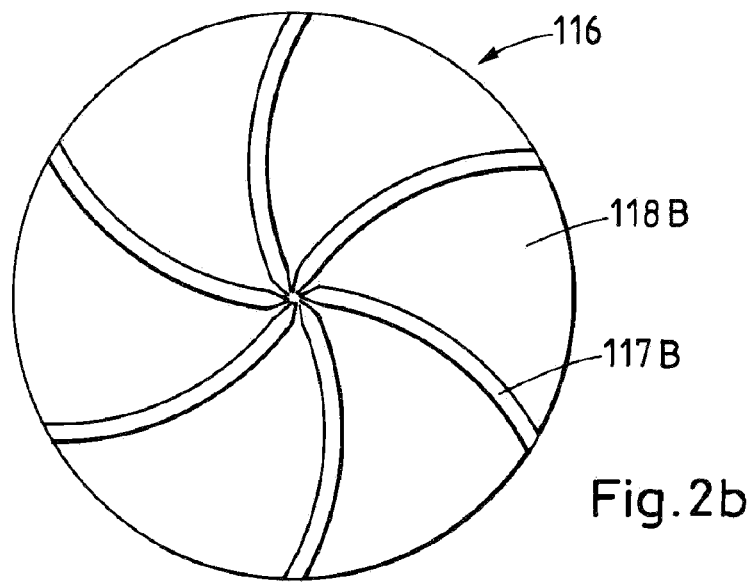
FIG. 2b is a bottom plan view of the radiation-releasing surface of FIG. 2a, seen in the direction X that is indicated in FIG. 2a, with a first configuration of the ridges.

The heat conductor 116 shown in FIG. 2b has narrow protruding ridges 117B of rectangular cross-section. These ridges 117B are curved in the radial direction. Accordingly the depressed areas 118B that are separated from each other by the ridges 117B are likewise curved in the radial direction. As is known from pumps and ventilation fans, the curvature makes it possible to choose the radial flow velocity as needed. As a result, stagnant accumulations of the gaseous medium between the ridges 117B, which could cause excessive turbulence between the sample and the radiation-releasing surface, can be prevented. Turbulences of this kind could critically influence the measuring result determined by the weighing cell. Of course, it is also possible that only a single ridge is formed on the radiation-releasing surface, with the single ridge being strongly curved in the radial direction so that it forms a spiral on the radiation-releasing surface.

Figure 2C:
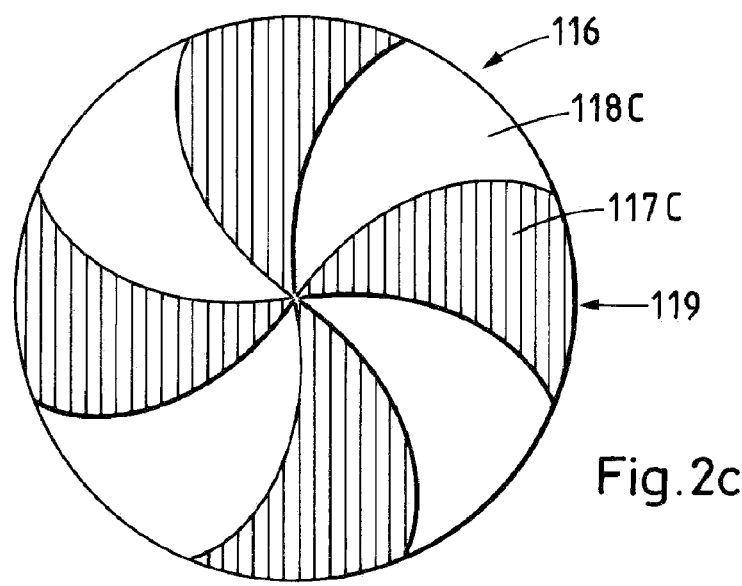
FIG. 2c is a further bottom plan view of the radiation-releasing surface of FIG. 2a, seen in the direction X that is indicated in FIG. 2a, with a second configuration of the ridges.

The heat conductor 116 shown in FIG. 2c is likewise equipped with protruding ridges 117c, which are shaded in the drawing for better clarity. However, unlike the ridges in FIG. 2b, the width of the ridges 117c gets continuously larger towards the border 119 of the heat conductor 116, so that the raised surfaces of the ridges 117C are equal to the depressed surface areas 118C which are formed between the ridges 117C. This results in a further improvement in the uniformity of the radiation intensity in comparison to the embodiment shown in FIG. 2b. The ridges 117C and depressions 118C are likewise curved in the radial direction as described in detail for FIG. 2b.

A further embodiment is illustrated schematically in FIG. 3a. A heat conductor 216 which is shown in a cross-sectional view includes an integrally incorporated radiator 211. The heat conductor 216 has an asymmetric configuration relative to the axis of rotation and the shaft 213. In order to achieve a uniform distribution of the radiation, the heat conductor 216 is designed with more mass towards the radiation-releasing surface 212. The radiator 211, for example a heating foil, can possibly also be set on top of the heat conductor 216.

FIG. 3b schematically illustrates the heat conductor 216 from FIG. 3a in a plan view as seen in the direction indicated by the arrow Z in FIG. 3a. The heat conductor 216 has the shape of a sector of a circle. This configuration avoids the problem that the radiation density in the vicinity of the shaft 213 is higher than towards the border 219, as the tangential velocity near the border 219 is naturally higher than in the vicinity of the shaft 213. The radiator 211 is shaped with a triangular outline and is completely imbedded in the heat conductor 216, as described in the context of FIG. 3a. In regard to the flow of energy or the delivery of the radiation to the sample, the embodiment shown in FIGS. 3a and 3b with this imbedded arrangement can likewise be said to have a rotatably supported heat conductor 216 arranged between the radiator 211 and the sample.

Figure 4:
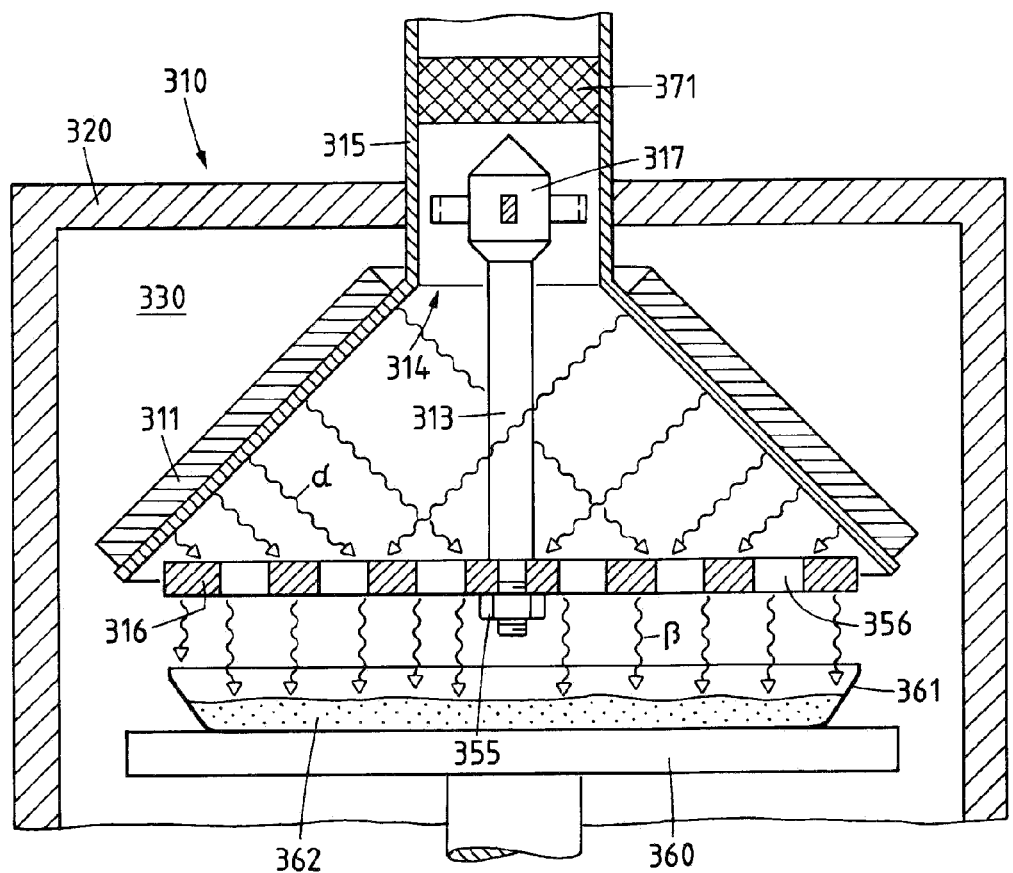
FIG. 4 is a side sectional view of a further embodiment, showing only the test compartment of the measuring instrument with a radiator, a sample, a sample receiver, a shaft, and a heat conductor, the latter being provided with perforations and connected to the shaft through a releasable fastener element.

FIG. 4 shows a further embodiment of a measuring instrument 310 according to the invention. A carrier body of a funnel-shaped, rotationally symmetric configuration is in the area of its narrow opening 314 connected to the housing 320 that surrounds the test compartment 330. The symmetry axis of the carrier body 315 is oriented in the direction of the load, and the narrow-diameter opening 314 faces against the direction of the load. Arranged on the cone-shaped outside surface of the carrier body 315 are radiators 311 emitting rays $\alpha$ which are directed against a rotatably arranged disk-shaped heat conductor 316 as indicated in FIG. 4. The heat conductor 316 is connected through a releasable connector element 355 to a shaft 313. The shaft 313 is driven by a drive source 317 which is arranged in the narrow opening 314. The releasable connector element 355 is shown as a screw connection, but one could, of course, also use any other known releasable and non-releasable connector elements.

As a result of having the heat conductor 316 arranged between the radiator 311 and the sample 362, the radiation $\alpha$ emitted by the radiators 311 is absorbed by the heat conductor 316. The heat conductor 316 delivers the absorbed energy as heat radiation $\beta$ to the sample 362. As may already be concluded from the different symbols, the radiations $\alpha$ and $\beta$ need not be of the same type of radiation. It is also possible that a conversion takes place in the heat conductor 316, for example by converting electromagnetic waves (microwaves, induction) into heat radiation.

The disk-shaped, rotationally symmetric heat conductor 316 has a plurality of perforations 356 allowing the passage of the heated and moisture-saturated gaseous medium so that it can leave the test compartment 330 through the narrow opening 314. This prevents that a moisture-saturated gas cushion could remain trapped between the heat conductor 316 and the sample 362. Since samples 362 can also contain solvents or other highly volatile components, it is possible that further volatile components are driven out of the sample 362 during the drying process, which could for example have a strong odor, or which could be toxic or corrosive. The narrow opening 314 of the carrier body 315 which serves as exhaust channel is therefore preferably equipped with a condenser 371 in which the moisture and/or volatile substance that has left the sample 362 is precipitated by means of cooling after it has left the test compartment. Instead of or in addition to the condenser, the narrow opening 314 can have a chemical filter. In a particularly preferred embodiment, the filter includes an adsorption agent, for example activated charcoal. The sample 362 is spread on a sample tray 361. The latter, in turn, rests on the sample receiver 360 which is shown in FIG. 4 as a conventional weighing pan of a balance.

Figure 5:
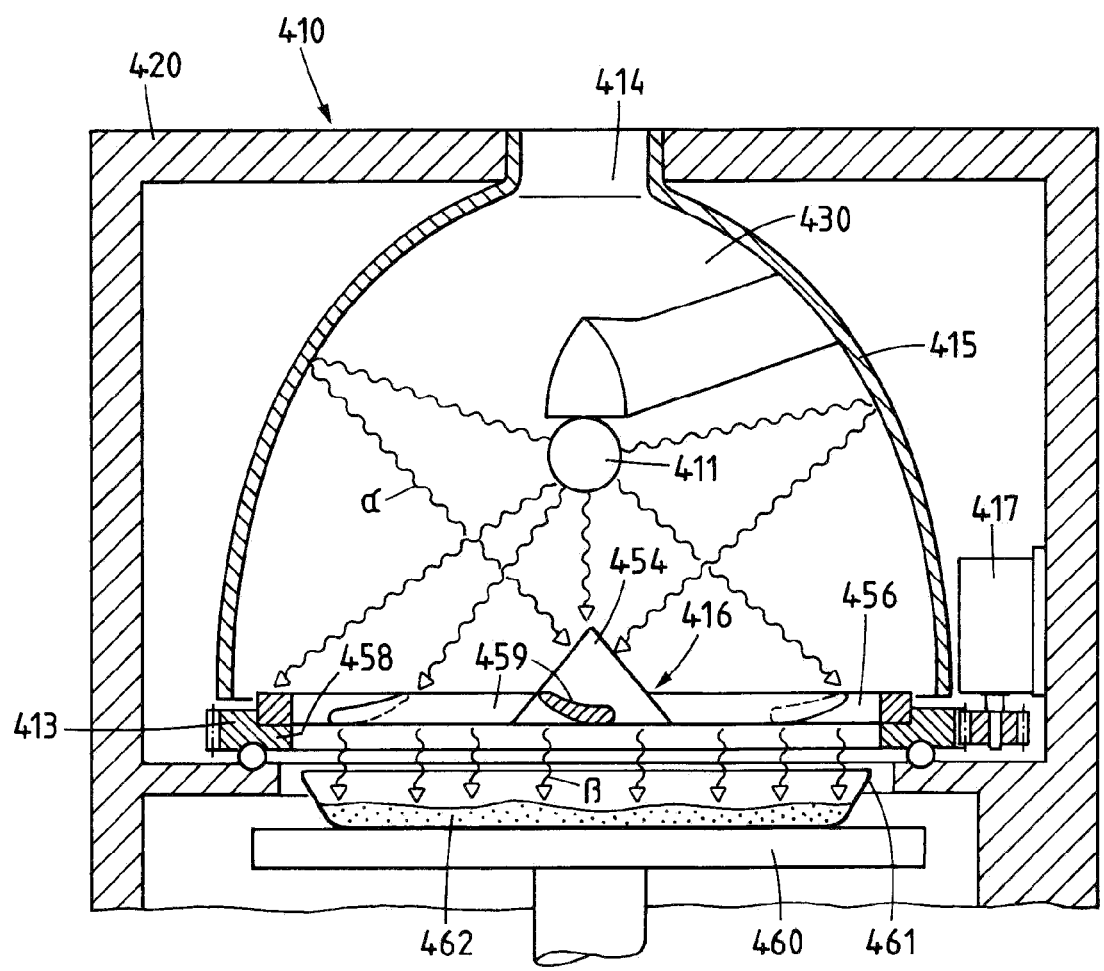
FIG. 5 is a side sectional view of a further embodiment, wherein only the test compartment of the measuring instrument is shown with a radiator, a radiation-guiding body, a sample, a sample receiver, and a roller-ball supported turntable with a heat conductor set in place.

FIG. 5 shows as a further embodiment of the invention a measuring instrument 410. A rotationally symmetric radiation-guiding body 415 has a narrow opening 414 and is connected near said opening to the housing 420 that encloses the sample compartment 430. The radiation-guiding body 415 has a symmetry axis oriented in the direction of the load, and the narrow-diameter opening 414 faces against the direction of the load. The inside of the radiation-guiding body 415 is provided with a radiation-reflecting surface which is not shown in the drawing. Arranged in the focal point of the radiation-guiding body 415 is a radiator 411 emitting rays $\alpha$ in all directions, as indicated in FIG. 5, with the reflective surface directing a part of the radiation $\alpha$ towards the mid-portion of a disk-shaped heat conductor 416. The heat conductor 416 has a form-fitting releasable connection to a turntable 413 supported by roller balls. The movable part of the turntable 413 is driven by a drive source 417 which is arranged between the housing 420 and the radiation-guiding body 415. The torque can be transmitted from the drive source 417 to the turntable 413 through contact between a pair of friction wheels or through the form-fitting contact between toothed gears as shown in the drawing. In the arrangement shown in FIG. 5, the heat conductor 416 is loosely seated on a ledge 458 formed on the inside of the turntable ring 413. Of course, the heat conductor 416 can also be secured by means of releasable connector elements against falling out or being displaced.

As a result of having the heat conductor 416 arranged between the radiator 411 and the sample 462, the radiation $\alpha$ emitted by the radiators 411 is absorbed by the heat conductor 416. The heat conductor 416 delivers the absorbed energy as heat radiation $\beta$ to the sample 462.

The disk-shaped, rotationally symmetric heat conductor 416 has a plurality of perforations 456 allowing the passage of the heated and moisture-saturated gaseous medium and allowing it to leave the test compartment 430 through the narrow opening 414. As a result of the perforations 456, three transverse members 459 are formed which have a favorable profile to enhance the flow movement. Thus, the three transverse members 459 serve not only as radiation-releasing surface towards the sample 462 but simultaneously support the removal of moisture from the vicinity of the sample 462. If the rate of rotation of the heat conductor 416 is small, it is possible to produce a nearly laminar flow and/or a slightly reduced pressure in the space between the sample 462 and the heat conductor 416. Arranged in the middle of the heat conductor 416 is a cone-shaped absorber body 454 which serves as connector element for the transverse members 459 and forms the target for the radiation $\alpha$ that is reflected by the radiation-guiding body 415. The sample 462 is spread on a sample tray 461. The latter, in turn, rests on the sample receiver 460, which is again shown in FIG. 5 as a conventional weighing pan of a balance.

The embodiments presented here show measuring instruments for the gravimetric determination of moisture content with different properties and features. In the interest of clarity, the different properties and features have been shown in different embodiments, but it is also possible to realize a combination of the proposed features and properties in a measuring instrument. Furthermore, solutions in which the shaft does not pass through an opening in the radiator but runs outside of the radiator are likewise within the scope of the invention. Nor is the invention limited to configurations with only one shaft. Furthermore, a continuous rotary movement is not a necessary condition for the invention to perform its function; it is also possible and within the scope of the invention that the shaft and/or the radiation-releasing surface oscillates back and forth. The scope of the invention is not limited to the configuration of the weighing cell and the housing as shown in FIG. 1, but can be used in all known measuring instruments that have radiators arranged above the sample.

What is claimed is:

1. A measuring instrument for gravimetric moisture determination of a sample, comprising:
    a weighing cell;
    a sample receiver, adapted for placement of the sample thereon and removal of the sample therefrom and for connection to the weighing cell;
    a radiator, arranged above the sample relative to a load direction of the weighing cell; and
    a rotatably-supported heat conductor, arranged between the radiator and the sample, the axis of rotation of the heat conductor being oriented orthogonal to the plane in which the sample or the sample receiver extends, so that the heat conductor absorbs at least part of the radiation from the radiator and releases part of the absorbed radiation as heat radiation to the sample through a radiation-releasing surface thereof, the rotation of the heat conductor permitting irradiation of the entire surface of the sample.

2. The measuring instrument of claim 1, wherein:
    the heat conductor substantially extends in a plane that is orthogonal to the axis of rotation, the radiation-releasing surface thereof substantially coinciding with the surface area of the heat conductor that faces towards the sample.

3. The measuring instrument of claim 2, wherein:
    the axis of rotation of the heat conductor is parallel to the load direction.

4. The measuring instrument of claim 3, wherein:
    the radiation-releasing surface comprises a circular sector.

5. The measuring instrument of claim 4, wherein:
    the radiation-releasing surface is perforated, incised or comprises a porous material, to allow gas to pass therethrough in the load direction.

6. The measuring instrument of claim 5, wherein:
    a transverse member is formed on the heat conductor with a shape analogous to a propeller blade or a scoop, such that rotation of the heat conductor directs gas flow, preferably directed against the load direction.

7. The measuring instrument of claim 6, wherein:
    the radiation-releasing surface has at least one protruding ridge, groove, channel or depression.

8. The measuring instrument of claim 7, wherein:
    the heat conductor comprises aluminum, aluminum alloys, iron, a ceramic material, or glass.

9. The measuring instrument of claim 1, further comprising:
    a drive source; and
    a shaft, driven by the drive source and connected to the heat conductor, the shaft supported by one or more bearings rigidly connected to a housing of the instrument.

10. The measuring instrument of claim 9, further comprising:
    releasable connector elements that connect the heat conductor to the shaft.

11. The measuring instrument of claim 1, wherein:
    the radiator is selected from the group consisting of a heating plate, a heating foil, a heat radiator, an induction coil, a halogen lamp, and a quartz lamp.

12. The measuring instrument of claim 1, further comprising:
    a radiation-guiding body within which the radiator is arranged.

13. The measuring instrument of claim 12, wherein:
    the radiation-guiding body is a flat metal plate that focuses the radiation of the radiator on the heat conductor.

14. The measuring instrument of claim 1, wherein:
    the axis of rotation of the heat conductor is parallel to the load direction.

15. The measuring instrument of claims 1, wherein:
    the radiation-releasing surface comprises a circular sector.

16. The measuring instrument of claim 1, wherein:
    the radiation-releasing surface has at least one protruding ridge, groove, channel or depression.

17. The measuring instrument of claim 1, further comprising:
    a drive source; and
    a turntable, driven through a gear stage by the drive source and connected to the heat conductor, the turntable supported by one or more roller balls.

18. The measuring instrument of claim 17, further comprising:
    releasable connector elements that connect the heat conductor to the turntable.

19. The measuring instrument of claim 12, wherein:
    the radiation-guiding body is open on at least one side with an interior provided with a reflective surface that focuses the radiation of the radiator on the heat conductor.

* * * * *

UNITED STATES PATENT AND TRADEMARK OFFICE
CERTIFICATE OF CORRECTION

| | | |
|---|---|---|
| PATENT NO. | : 7,735,355 B2 | |
| APPLICATION NO. | : 11/769460 | |
| DATED | : June 15, 2010 | |
| INVENTOR(S) | : Lüchinger | |

It is certified that error appears in the above-identified patent and that said Letters Patent is hereby corrected as shown below:

On the title page, section (74), Attorney, Agent, or Firm, please delete "Stanley Law Group LLP" and insert -- Standley Law Group LLP --.

In column 2, line 23, please delete "he" and insert -- the --.

In column 8, line 35, please delete "11 7B" and insert -- 117B --.

In column 12, line 28, please delete "claims 1" and insert -- claim 1 --.

Signed and Sealed this

Thirty-first Day of August, 2010

David J. Kappos
*Director of the United States Patent and Trademark Office*